(12) United States Patent
Chehebar et al.

(10) Patent No.: US 11,504,332 B2
(45) Date of Patent: Nov. 22, 2022

(54) PHOSPHODIESTERASE-4 INHIBITOR COMBINATIONS, METHODS OF MAKING, AND METHODS OF USE THEREOF

(71) Applicant: VK RESEARCH ASSOCIATES INC., Dover, DE (US)

(72) Inventors: Victor Chehebar, Massapequa, NY (US); Siva Rama Krishna Nutalapati, Princeton, NJ (US)

(73) Assignee: VK RESEARCH ASSOCIATES INC., Dover, DE (US)

( * ) Notice: Subject to any disclaimer, the term of this patent is extended or adjusted under 35 U.S.C. 154(b) by 0 days.

(21) Appl. No.: 17/402,747

(22) Filed: Aug. 16, 2021

(65) Prior Publication Data

US 2022/0304935 A1    Sep. 29, 2022

Related U.S. Application Data

(60) Provisional application No. 63/164,706, filed on Mar. 23, 2021.

(51) Int. Cl.

| | |
|---|---|
| *A61K 31/138* | (2006.01) |
| *A61K 9/20* | (2006.01) |
| *A61K 9/00* | (2006.01) |
| *A61K 45/06* | (2006.01) |
| *A61K 31/4015* | (2006.01) |
| *A61K 31/4375* | (2006.01) |
| *A61K 31/277* | (2006.01) |
| *A61K 31/192* | (2006.01) |

(52) U.S. Cl.
CPC .......... *A61K 9/2027* (2013.01); *A61K 9/0053* (2013.01); *A61K 9/2013* (2013.01); *A61K 9/2054* (2013.01); *A61K 31/138* (2013.01); *A61K 31/192* (2013.01); *A61K 31/277* (2013.01); *A61K 31/4015* (2013.01); *A61K 31/4375* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,696,066 | B2 * | 2/2004 | Kaiko | A61K 45/06 |
| | | | | 424/464 |
| 6,713,509 | B1 * | 3/2004 | Faulkner | A61K 9/2027 |
| | | | | 514/525 |
| 2006/0269600 | A1 * | 11/2006 | Dietrich | A61K 31/44 |
| | | | | 424/464 |
| 2008/0261991 | A1 * | 10/2008 | Bar-Or | A61K 31/485 |
| | | | | 514/252.16 |
| 2012/0088743 | A1 * | 4/2012 | Gras Escardo | A61K 31/196 |
| | | | | 514/171 |
| 2021/0275531 | A1 * | 9/2021 | Nutalapati | A61K 47/26 |

FOREIGN PATENT DOCUMENTS

WO    WO-2020148271 A1 *    7/2020    ......... A61K 31/4436

OTHER PUBLICATIONS

A. Robichaud, et al, Emesis Induced by Inhibitors of Type IV Cyclic Nucleotide Phosphodiesterase (PDE IV) in the Ferret, 38 NEUROPHARMACOL. 289 (Year: 1999).*
Tim Vanmierlo, et al, The PDE4 Inhibitor Roflumilast Improves Memory in Rodents at Non-Emetic Doses, 303 Behav. Brain Res. 26 (Year: 2016).*

* cited by examiner

*Primary Examiner* — Sean M Basquill
(74) *Attorney, Agent, or Firm* — Licata & Tyrrell P.C.

(57) ABSTRACT

Compositions and kits for oral administration of a phosphodiesterase-4 (PDE4) inhibitor and one or more additional active agents that reduces or eliminates a side effect associated with the PDE4 inhibitor are provided. Also provided are methods for use of these compositions and kits for treating conditions treatable with a PDE4 inhibitor therapy and for increasing patient compliance with treatment with PDE4 inhibitors.

11 Claims, No Drawings

PHOSPHODIESTERASE-4 INHIBITOR COMBINATIONS, METHODS OF MAKING, AND METHODS OF USE THEREOF

This patent application claims the benefit of priority from U.S. Provisional Application Ser. No. 63/164,706, filed Mar. 23, 2021, the teachings of which are incorporated by reference in their entirety.

FIELD

This disclosure relates to compositions and kits for oral administration of a phosphodiesterase-4 (PDE4) inhibitor and one or more additional active agents that reduces or eliminates a side effect associated with the PDE4 inhibitor. Methods for use of these compositions and kits for treating conditions treatable with a PDE4 inhibitor therapy and increasing patient compliance with treatment with PDE4 inhibitors are also disclosed.

BACKGROUND

Phosphodiesterase-4 (PDE4), mainly present in immune cells, epithelial cells, and brain cells, manifests as an intracellular non-receptor enzyme that modulates inflammation and epithelial integrity. Inhibition of PDE4 is predicted to have diverse effects via the elevation of the level of cyclic adenosine monophosphate (cAMP) and the subsequent regulation of a wide array of genes and proteins. PDE4 has been identified as a promising therapeutic target for the treatment of diverse pulmonary, dermatological, and severe neurological diseases. Over the past decades, numerous PDE4 inhibitors have been designed and synthesized, among which Roflumilast, Apremilast, and Crisaborole were approved for the treatment of inflammatory airway diseases, psoriatic arthritis, and atopic dermatitis, respectively. Increasing evidence show that PDE4 inhibitors may be useful in the treatment of multiple sclerosis, Behcet's syndrome and autoimmune diseases. However, the efficacies of these drugs are often accompanied by adverse effects, such as nausea, emesis, diarrhea, headache, dyspepsia and upper respiratory tract infections.

The dose limiting side effects have tempered the enthusiasm of this drug class for the treatment of these diseases. A number of strategies are currently being pursued in attempts to improve clinical efficacy and reduce side effects, including delivery via the inhaled route, and/or development of non-emetic PDE4 inhibitors and mixed PDE inhibitors.

There remains a need for methods and treatments that can lessen the severity of, or even prevent, side effects associated with PDE4 inhibitor therapy.

SUMMARY

An aspect of this disclosure relates to compositions for oral administration of a phosphodiesterase-4 (PDE4) inhibitor in combination with one or more additional active agents that reduces or eliminates a side effect associated with the PDE4 inhibitor. Compositions of this disclosure may be formulated to release each of the phosphodiesterase-4 (PDE4) inhibitor and the additional active agent as immediate release or controlled release or a combination of both immediate release and controlled release.

In one nonlimiting embodiment, the PDE4 inhibitor is Roflumilast, Apremilast, Crisaborole, Cilomilast, Ronomilast, Oglemilast, Rolipram, Piclamilast, Ibudilast, Tetomilast, Revamilast, Roflumilast, Tofimilast, Almiral, Lotamilast or a combination thereof.

In one nonlimiting embodiment, the additional active agent is an analgesic, an anti-bacterial agent, an anti-nausea agent, an antiemetic, an anti-diarrheal, a proton pump inhibitor, an antacid, an anti-gas agent, an anti-anxiety agent, an anti-depressant, an appetite stimulant, an agent to treat insomnia or any combination thereof.

Another aspect of this disclosure relates to kits comprising a PDE4 inhibitor and one or more additional active agents that reduces or eliminates a side effect associated with the selected PDE4 inhibitor. In these kits, the PDE4 inhibitor and one or more additional active agents can be formulated for immediate release or controlled release or a combination of both immediate release and controlled release.

In one nonlimiting embodiment, the PDE4 inhibitor is Roflumilast, Apremilast, Crisaborole, Cilomilast, Ronomilast, Oglemilast, Rolipram, Piclamilast, Ibudilast, Tetomilast, Revamilast, Roflumilast, Tofimilast, Almiral, Lotamilast or a combination thereof.

In one nonlimiting embodiment, the additional active agent is an analgesic, an anti-bacterial agent, an anti-nausea agent, an antiemetic, an anti-diarrheal, a proton pump inhibitor, an antacid, an anti-gas agent, an anti-anxiety agent, an anti-depressant, an appetite stimulant, an agent to treat insomnia or any combination thereof.

Another aspect of this disclosure relates to methods for treating conditions treatable with a PDE4 inhibitor with these compositions and kits.

Yet another aspect of this disclosure relates to methods for increasing patient compliance with treatment with a PDE4 inhibitor with these compositions and kits.

DETAILED DESCRIPTION

The onset, severity and duration of side effects are PDE4 inhibitor specific. Thus, there is a need for PDE4 treatments tailored to the specific PDE4 inhibitor and the particular adverse effect caused by the PDE4 inhibitor.

Disclosed herein are combination oral therapies that allow for the convenience of receiving PDE4 inhibitor therapy while at the same time eliminating, or significantly reducing the severity of, side effects commonly associated with PDE4 inhibitor therapy, including the most bothersome side effects of headache, nausea, vomiting, diarrhea, dyspepsia, and respiratory tract infections. The combination formulations, kits, and dosing regimens disclosed herein comprise a PDE4 inhibitor and one or more additional active agents that provides the necessary relief from adverse symptoms in the convenience of a single oral dosage form comprising all of the active agents, or separate oral dosage forms of each active agent conveniently packaged together as a kit for concomitant administration. In addition to be useful in treating conditions treatable with a PDE4 inhibitor, the compositions and kits disclosed herein have the additional beneficial effect of improving patient compliance with PDE4 inhibitor therapy by reducing or eliminating side effects.

The combination oral therapies disclosed herein allow for a tailoring of the PDE4 inhibitor treatment and control of side effects, taking into account the particular PDE4 inhibitor, its particular pharmacokinetic properties, whether the dosing is chronic or acute, the dosage strength used, and the particular adverse effect caused by the same, including the onset and duration of a particular adverse effect.

A few of the most bothersome side effects from PDE4 inhibitor therapy noted in multiple studies are headache, nausea, vomiting, diarrhea, dyspepsia and respiratory tract infections. Most patients do not carry or have analgesic or anti-nausea or antiemetic or an acid reducer or anti-diarrheal medications readily available and have experienced any or some of these side effects, which either lead to the discontinuation of these PDE4 inhibitors or resultant pain and suffering.

In this disclosure, combination therapies which reduce PDE4 side effects are achieved by correlating the therapeutic effect of the additional active agent with the pharmacokinetic characteristics of the particular PDE4 inhibitor used, specifically by modifying the release and duration of the additional active agent through tailored formulation.

In one nonlimiting embodiment, a composition for oral administration is provided comprising a PDE4 inhibitor and one or more additional active agents that can reduce or eliminate a side effect associated with PDE4 inhibitor, wherein the additional active agent is an analgesic, an anti-bacterial agent, an anti-nausea agent, an antiemetic, an anti-diarrheal, a proton pump inhibitor, an antacid, an anti-gas agent, an anti-anxiety agent, an anti-depressant, an appetite stimulant, an agent to treat insomnia or a combination thereof.

In another nonlimiting embodiment, a kit is provided comprising an oral formulation of PDE4 inhibitor and a separate oral formulation of one or more additional active agents that can reduce or eliminate a side effect associated with the PDE4 inhibitor.

In one nonlimiting embodiment, the additional active agent is an analgesic. In one nonlimiting embodiment, the analgesic is a non-steroidal, anti-inflammatory or a pharmaceutically acceptable salt thereof. Nonlimiting examples of analgesics include acemetacin, acetaminophen, aminoprofen, aspirin, benoxaprofen, bucloxic acid, carisoprodol, carprofen, celecoxib, clidanac, cyclobenzaprine, diclofenac, diflurisal, fentiazac, flufenamic acid, flurbiprofen, fenoprofen, flubufen, flufenisal, isoxicam, ketoprofen, ibuprofen, indomethacin, indoprofen, ketorolac, naproxen, nabumetone, meclofenamic acid, meclofenate, mefenamic acid, metaxalone, methocarbamol, muroprofen, niflumic acid, orphenadrine, oxaprozin, oxpinac, piroprofen, piroxicam, pramoprofen, sudoxicam, sulindac, suprofen, tiaprofenic acid, tiopinac, tolmetin, tolfenamic acid, trioxaprofen, zidometacin, zomepirac, or a pharmaceutically acceptable salt thereof. In one nonlimiting embodiment, the analgesic is naproxen sodium, orphenadrine citrate, or a combination thereof;

In one nonlimiting embodiment, the additional active agent is an anti-bacterial agent such as, but not limited to, a pharmaceutically acceptable penicillin, a pharmaceutically acceptable cephalosporin, a pharmaceutically acceptable aminoglycoside, a pharmaceutically acceptable tetracycline, a pharmaceutically acceptable macrolide, a pharmaceutically acceptable fluoroquinolone or a combination thereof.

In one nonlimiting embodiment, the additional active agent is an anti-nausea or antiemetic agent such as, but not limited to, an antihistamine such as Meclizine HCl or Dimenhydrinate, Bismuth subsalicylate, Emetrol, Ondonsetron, Dolasetron, Granisetron, Palanosetron, Promethazine, Metoclopramide, Procloperazine, Hydroxyzine, Lorazepam, Aprepitant, Dexamethasone, a pharmaceutically acceptable salt thereof, or a combination thereof.

In one nonlimiting embodiment, the additional active agent is an anti-diarrheal agent such as, but not limited to, Loperamide, Bismuth subsalicylate, Alosetron, Eluxadoline, Rifaximin, a pharmaceutically acceptable salt thereof, or a combination thereof.

In one nonlimiting embodiment, the additional active agent is a proton pump inhibitor such as, but not limited to, esomeprazole magnesium, esomeprazole sodium, esomeprazole strontium, dexlansoprazole, lansoprazole, omeprazole magnesium, omeprazole sodium, omeprazole strontium, pantoprazole sodium, rabeprazole sodium, or a combination thereof.

In one nonlimiting embodiment, the additional active agent is a H2 blocker such as, but not limited to, cimetidine, famotidine, nizatidine, ranitidine, a pharmaceutically acceptable salt thereof, or a combination thereof. In one nonlimiting embodiment, the H2 block is cimetidine hydrochloride, famotidine, nizatidine, ranitidine hydrochloride, or a combination thereof.

In one nonlimiting embodiment, the additional active agent is an antacid such as, but not limited to, a pharmaceutically acceptable alkali or alkaline earth metal carbonate, a pharmaceutically acceptable alkali or alkaline earth metal hydroxide, or a combination thereof, specifically calcium carbonate, magnesium carbonate, sodium bicarbonate, aluminum hydroxide, magnesium hydroxide, or a combination thereof;

In one nonlimiting embodiment, the additional active agent is an anti-gas agent such as simethicone.

In one nonlimiting embodiment, the additional active agent is an anti-anxiety agent such as, but not limited to, a pharmaceutically acceptable Benzodiazepine (Diazepam, Lorazepam, Alprazolam, Clonazepam), Buspirone, a pharmaceutically acceptable antidepressant (Escitalopram, Fluoxetine, Sertraline, Paroxetine, Imipramine, Chlorimipramine, Isocarboxazid, Phenelzine, Selegiline), a beta blocker or a combination thereof.

In one nonlimiting embodiment, the additional active agent is an anti-depressant such as, but not limited to, is Escitalopram, Fluoxetine, Sertraline, Paroxetine, Imipramine, Chlorimipramine, Isocarboxazid, Phenelzine, Selegiline, a pharmaceutically acceptable salt thereof, or a combination thereof;

In one nonlimiting embodiment, the additional active agent is an appetite stimulant such as, but not limited to, Megestrol, Oxandrolone, Dronabinol, Prednisone, and Dexamethasone, a pharmaceutically acceptable salt thereof or a combination thereof.

In one nonlimiting embodiment, the additional active agent is used to treat insomnia. Nonlimiting examples include Diazepam, Lorazepam, Alprazolam, Clonazepam, Triazolam, Estazolam, Zolpidem, Eszopiclone, Zaleplon, Belsomra, Doxepin, and Ramelteon, a pharmaceutically acceptable salt thereof or a combination thereof.

As a nonlimiting example of a combination of this disclosure, oral administration of PDE4 inhibitor Rolipram has a half-life of about 3 hours and achieves a median time to maximum concentration at about 30 minutes. Any side effect from acute Rolipram therapy appears quickly and lasts for a few hours. Thus, it would be advantageous to have the additional active agent, such as an analgesic, in an immediate release form, in order to effectively manage headache, a side effect from Rolipram treatment.

As another nonlimiting example, oral administration of Roflumilast has a half-life of 17 to 30 hours and achieves a median time to maximum concentration at about 1 to 2 hours. Any side effect from acute Roflumilast therapy appears later as compared to Rolipram and continues for several hours longer. Thus, when Roflumilast is the PDE4 inhibitor, it may be more appropriate to have the analgesic additional active agent in an extended release form in order to effectively manage a reduction or elimination of a side effect from Roflumilast treatment, which would be expected to occur later following administration and to last for a longer duration.

As exemplified, the release of the additional active agent from the combination can be tailored depending upon the PDE4 inhibitor type and strength used in the combination and the particular adverse effect to be targeted. Use of an extended release analgesic, such as extended release acetaminophen or naproxen, can be used to prevent or lessen headache and body pain side effects caused by Roflumilast. Mild headaches can be addressed with shorter acting combinations of analgesics and PDE4 inhibitors such as an immediate release form of each active agent.

Half-lives for nonlimiting of examples of PDE4 inhibitors which can be used in compositions and kits of this disclosure are depicted in Table 1.

TABLE 1

| PDE 4 Inhibitor | Median plasma/elimination Half-life (T1/2) |
| --- | --- |
| Rolipram | 3 |
| Apremilast | 6 to 9 |
| Cilomilast | 7 |
| Crisaborole | 11.9 ± 8.3 |
| Ibudilast | 19 |
| Roflumilast | 17-30 |

Nonlimiting examples of side effects which occur from administration of PDE4 inhibitors and additional active agents which can be included in the compositions and kits of this disclosure are listed in Table 2.

TABLE 2

| Side effect | Drug combination |
| --- | --- |
| Headache | NSAIDs (Ibuprofen, Naproxen), Acetaminophen, Aspirin, Celecoxib, a pharmaceutically acceptable salt thereof |
| Nausea and Vomiting | Antihistamines: Meclizine HCl, Dimenhydrinate, a pharmaceutically acceptable salt thereof Bismuth subsalicylate, Emetrol, a pharmaceutically acceptable salt thereof Ondonsetron, Dolasetron, Granisetron, Palanosetron, Promethazine, Metoclopramide, Procloperazine, Hydroxyzine, Lorazepam, a pharmaceutically acceptable salt thereof Aprepitant, Dexamethasone, a pharmaceutically acceptable salt thereof |
| Diarrhea | Loperamide, Bismuth subsalicylate, a pharmaceutically acceptable salt thereof Alosetron, Eluxadoline, Rifaximin, a pharmaceutically acceptable salt thereof |
| Nervousness and Anxiety | Benzodiazepines: Diazepam, Lorazepam, Alprazolam, Clonazepam, a pharmaceutically acceptable salt thereof Buspirone, a pharmaceutically acceptable salt thereof Antidepressants: SSRI (Escitalopram, Fluoxetine, Sertraline, Paroxetine), Tricyclics (Imipramine, Chlorimipramine), MAOIs (Isocarboxazid, Phenelzine, Selegiline), Beta blockers, a pharmaceutically acceptable salt thereof |
| Insomnia | Benzodiazepines: Diazepam, Lorazepam, Alprazolam, Clonazepam Triazolam, Estazolam, a pharmaceutically acceptable salt thereof |

TABLE 2-continued

| Side effect | Drug combination |
| --- | --- |
| Dyspepsia | Zolpidem, Eszopiclone, Zaleplon Belsomra, Doxepin, Ramelteon, a pharmaceutically acceptable salt thereof Antihistamines Proton pump inhibitors (esomeprazole, dexlansoprazole, lansoprazole, omeprazole, pantoprazole, rabeprazole, a pharmaceutically acceptable salt thereof), H2 blockers (cimetidine, famotidine, nizatidine, ranitidine, a pharmaceutically acceptable salt thereof) Antacids (calcium carbonate, magnesium carbonate, sodium bicarbonate, aluminum hydroxide, magnesium hydroxide, or a combination thereof) |
| Antibacterial agent | Penicillins, cephalosporins, aminoglycosides, tetracyclines, macrolides, fluoroquinolones, or a combination thereof |
| Depressed mood | Antidepressants: SSRI (Escitalopram, Fluoxetine, Sertraline, Paroxetine, a pharmaceutically acceptable salt thereof), Tricyclics (Imipramine, Clomipramine, a pharmaceutically acceptable salt thereof), MAOIs (Isocarboxazid, Phenelzine, Selegiline, a pharmaceutically acceptable salt thereof) |
| Weight Loss | Appetite stimulants: Megestrol, Oxandrolone, Dronabinol, a pharmaceutically acceptable salt thereof Steroids: Prednisone, Dexamethasone, a pharmaceutically acceptable salt thereof |

The PDE4 inhibitor combinations can be formulated for oral or buccal administration as a solid, liquid, or semisolid. "Oral dosage form" is meant to include a unit dosage form for oral administration. Exemplary solid oral and buccal dosage forms include tablets, capsules, pellets, films, sachets, powders, chewable gummies, and the like. Exemplary oral liquid dosage forms include solutions, suspensions, emulsions, and the like.

For a combination of immediate release and controlled release dosage form, the PDE4 inhibitor can be immediate release and each additional active agent can be controlled release; the PDE4 inhibitor can be controlled release and each additional active agent individually can be immediate release, controlled release, or a combination thereof; a first portion of the PDE4 inhibitor can be administered as immediate release and a second portion can be administered as controlled release, and each additional active agent individually can be immediate release, controlled release, or a combination thereof; or the PDE4 inhibitor can be immediate release, controlled release, or a combination thereof and each additional active agent individually can be administered with a first portion as immediate release and a second portion as controlled release.

By "immediate-release" it is meant a conventional or non-modified release in which greater than or equal to about 75% of the active agent is released within two hours of administration, specifically within one hour of administration, yet more specifically within 30 minutes of administration.

By "controlled-release", it is meant a dosage form in which the release of an active agent is controlled or modified over a period of time and does not include immediate-release. Controlled can mean, for example, extended/sustained release, delayed release, or pulsed release at a particular time.

By "sustained release" it is meant to include the release of the active agent (e.g., analgesic) at such a rate that blood (e.g., plasma) levels are maintained within a therapeutic range but below toxic levels for about 4 to 24 hours after administration at steady-state. The term "steady-state" means that a plasma level for a given drug has been achieved and which is maintained with subsequent doses of the drug at a level which is at or above the minimum effective therapeutic level and is below the minimum toxic plasma level for a given drug.

By "delayed release" it is meant to include the release of the active agent after a predetermined time lag before it begins to release drug.

By "pulsed release" it is meant to include an initial quick burst of drug release followed by a predetermined period of no release followed by a second burst of drug release.

Oral dosage forms of this disclosure can be a monolithic matrix tablet or a layered tablet having two or more layers wherein the PDE4 inhibitor and the additional active agent can be in separate layers or in the same layer; a capsule; a subunit form such as a plurality of granules, microtablets, minitablets, caplets, pellets (as used herein "pellet" means a spherical granule prepared by extrusion and spheronization, and is equivalent to bead, spheroid, and microsphere), particles, active agent cores, or other multiparticulate system, a plurality of which may optionally be encapsulated, e.g., in a hard gelatin capsule.

A solid, oral dosage form comprises a PDE4 inhibitor, an additional active agent, and a pharmaceutically acceptable excipient.

As used herein, "pharmaceutically acceptable excipient" means any other component added to the pharmaceutical formulation other than the active agent. Excipients may be added to facilitate manufacture, enhance stability, enhance product characteristics, enhance bioavailability, enhance patient acceptability, etc. Pharmaceutical excipients include carriers, fillers, binders, disintegrants, lubricants, glidants, granulating agents, compression aids, colors, release controlling agents, sweeteners, preservatives, suspending agents, dispersing agents, film formers, flavorants, printing inks, buffering agents, pH adjusters, preservatives, coatings, and the like. In some instances, a single material will meet two or more of the foregoing general classifications, e.g., depending upon the particular amount of the material employed.

Exemplary pharmaceutically acceptable excipients include fillers, such as a water insoluble filler, water soluble filler, or a combination thereof. The filler may be a water insoluble filler, such as carnauba wax, stearic acid, silicon dioxide, titanium dioxide, talc, alumina, starch, kaolin, polacrilin potassium, powdered cellulose, microcrystalline cellulose, sodium citrate, dicalcium phosphate, or a combination thereof. Exemplary water-soluble fillers include water soluble sugars and sugar alcohols, specifically lactose, glucose, fructose, sucrose, mannose, dextrose, galactose, the corresponding sugar alcohols and other sugar alcohols, such as mannitol, sorbitol, xylitol, or a combination thereof.

Exemplary binders include alginic acid, a carbomer, carboxymethylcellulose calcium, carboxymethylcellulose sodium, carrageenan, cellulose acetate phthalate, chitosan, ethyl cellulose, guar gum, hydroxyethyl cellulose, hydroxyethylmethyl cellulose, hydroxypropyl cellulose, hydroxypropyl methyl cellulose, methyl cellulose, microcrystalline cellulose, poloxamer, polyethylene oxide, polymethacrylates, polyvinylpyrrolidone ("povidone or PVP"), a saccharide, a starch, partially pregelatinized starch, and the like, or a combination thereof.

Release-retarding material for use in a controlled release solid, oral dosage form matrix formulation can include, for example, a hydrophobic cellulose polymer (e.g. ethylcellulose, hypromellose acetate succinate, cellulose acetate, cellulose acetate propionate, and the like, or a combination thereof); a hydrophilic cellulose polymer (e.g., methylcellulose, hydroxypropylmethylcellulose (HPMC), hydroxypropylcellulose (HPC), hydroxyethylcellulose (HEC), ethylhydroxyethylcellulose (E-HEC), sodium-carboxymethylcellulose (Na-CMC), and the like, or a combination thereof); a non-cellulosic material (e.g., sodium alginate, xanthan gum, carrageenan, chitosan, guar gum, pectin, polyethylene oxide, shellac, zein, and the like, or a combination thereof); a hydrophobic material (e.g., waxes, hydrogenated vegetable oil, hydrogenated castor oil, fatty acids, glyceryl monostearate, stearic acid, and the like); a pharmaceutically acceptable acrylic polymer; or a combination thereof. Generally the hydrophilic polymers and non-cellulosic material used as a controlled release matrix agent are swelling controlled release matrix systems, which control release rate of the active agent by the rate of penetration of media and erosion of the matrix.

Suitable pharmaceutically acceptable acrylic polymer for use as a release-retarding material include, for example, an acrylic acid and methacrylic acid copolymer, a methyl methacrylate copolymer, an ethoxyethyl methacrylate, a cyanoethyl methacrylate, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate, a polymethacrylate, a poly(methyl methacrylate) copolymer, a polyacrylamide, an aminoalkyl methacrylate copolymer, a glycidyl methacrylate copolymer, an ammonio methacrylate copolymer, and the like, or a combination thereof.

Exemplary disintegrants include alginic acid, carboxymethylcellulose calcium, carboxymethylcellulose sodium, cross-linked sodium carboxymethylcellulose (sodium croscarmellose), powdered cellulose, chitosan, croscarmellose sodium, crospovidone, guar gum, low substituted hydroxypropyl cellulose, methyl cellulose, sodium alginate, sodium starch glycolate, partially pregelatinized starch, pregelatinized starch, starch, sodium carboxymethyl starch, and the like, or a combination thereof.

Exemplary lubricants include calcium stearate, magnesium stearate, glyceryl behenate, glyceryl palmitostearate, hydrogenated castor oil, light mineral oil, sodium lauryl sulfate, magnesium lauryl sulfate, sodium stearyl fumarate, stearic acid, zinc stearate, or a combination thereof.

Exemplary glidants include colloidal silica, amorphous silica, precipitated silica, talc, calcium phosphate tribasic, calcium silicate, magnesium silicate, magnesium trisilicate, or a combination thereof.

The solid oral dosage forms can be prepared using equipment and techniques known in the art for tableting included direct compression, granulation, capsule filling, pelletizing, and the like. In common tableting processes, the material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. In a multi-layered embodiment, a bi-layer or tri-layer tablet press may be employed, for example, where each chamber is fed with different a different powder to produce two or three individual layers in the same tablet; or a die is first loaded with the first-layer powder followed by the second-layer powder, that upon compression produces a tablet having two distinct layers (loading a third-layer powder on the second-layer powder can product a tablet with three distinct layers).

The solid, oral dosage form can optionally be coated with a coating for any number of reasons. The coating can be a nonfunctional coating or a functional coating. As used herein, a nonfunctional coating is one that does not substantially affect the overall release profile of the active agent compared to the release profile of the uncoated core formulation. Such coatings can be used for decorative or appearance of the dosage form for identifying purposes (e.g. based on a certain color), patient convenience (ease of swallowing), taste-masking, product stability (protection from humidity, light, oxygen), and the like. A functional coating, as used herein, is a coating that provides controlled release of the active agent from the dosage form, including extended/sustained-release, delayed release, or pulsed release. Exemplary non-functional coatings include film coatings. Exemplary functional coatings include enteric coatings and coatings that can target release in a particular region of the gastrointestinal tract. The foregoing coatings may also be used in a multiparticulate system described herein.

In general, a film coating can comprise a water soluble film coating polymer, a plasticizer, a colorant, an additional coating agent such as talc, and the like.

In general, a functional coating can comprise a pH-dependent polymer such as an enteric polymer, a plasticizer, a colorant, an additional coating agent such as talc, and the like. Enteric polymers are predominantly soluble in the intestinal fluid, but substantially insoluble in the gastric juices. Suitable enteric coating polymers include, for example, polyvinyl acetate phthalate (PVAP), hydroxypropylmethyl-cellulose acetate succinate (HPMCAS), cellulose acetate phthalate (CAP), methacrylic acid copolymer, hydroxy propyl methylcellulose succinate, cellulose acetate succinate, cellulose acetate hexahydrophthalate, hydroxypropyl methylcellulose hexahydrophthalate, hydroxypropyl methylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT L, which is an anionic copolymer based on methacrylate and available as a powder, also known as methacrylic acid copolymer, type A (USP NF)), methacrylic acid-methyl methacrylate copolymer, ethyl methacrylate-methylmethacrylate-chlorotrimethylammonium ethyl methacrylate copolymer, methacrylic acid: acrylic acid ethyl ester 1:1 copolymer solid substance of the acrylic dispersion sold under the trade designation "Eudragit L-100-55", and the like, or a combination thereof. Other functional coating agents include for example, a hydrophobic cellulose polymer (e.g. ethylcellulose, hypromellose acetate succinate, cellulose acetate, cellulose acetate propionate, and the like, or a combination thereof); a hydrophilic cellulose polymer (e.g., methylcellulose, hydroxypropylmethylcellulose (HPMC), hydroxypropylcellulose (HPC), hydroxyethylcellulose (HEC), ethylhydroxyethylcellulose (E-HEC), sodium-carboxymethylcellulose (Na-CMC), and the like, or a combination thereof); a non-cellulosic material (e.g., sodium alginate, xanthan gum, carrageenan, chitosan, guar gum, pectin, polyethylene oxide, shellac, zein, and the like, or a combination thereof); a hydrophobic material (e.g., waxes, hydrogenated vegetable oil, hydrogenated castor oil, fatty acids, glyceryl monostearate, stearic acid, and the like); a pharmaceutically acceptable acrylic polymer; or a combination thereof.

The PDE4 inhibitor combinations can be formulated as a non-chewable, orally disintegrating tablet (alternatively referred to as "orally dispersible tablet"). These dosage forms can be made by methods known to those of ordinary skill in the art of pharmaceutical formulations.

An exemplary orally disintegrating tablet includes a mixture incorporating a water or saliva activated effervescent disintegration agent and the active agent. The mixture may be formulated as a tablet of a size and shape adapted for direct oral administration to a patient. The orally disintegrating tablet is substantially completely disintegrable upon exposure to water or saliva. The effervescent disintegration agent is present in an amount effective to aid in disintegration of the tablet, and to provide a distinct sensation of effervescence when the tablet is placed in the mouth of a patient.

Other types of orally disintegrating tablets can be prepared without an effervescent agent by using a spray dried carbohydrate or sugar alcohol excipients (e.g. sorbitol, mannitol, xylitol, or a combination thereof, and the like), optionally combined with a disintegrant (e.g. the disintegrant can be crospovidone, croscarmellose, sodium starch glycolate, pregelatinized starch, partially pregelatinized starch, or a combination thereof, and the like), or a glidant (e.g. colloidal silica, silica gel, precipitated silica, or a combination thereof, and the like).

Orally disintegrating tablets can be manufactured by well-known tableting procedures. In common tableting processes, the material which is to be tableted is deposited into a cavity, and one or more punch members are then advanced into the cavity and brought into intimate contact with the material to be pressed, whereupon compressive force is applied. The material is thus forced into conformity with the shape of the punches and the cavity.

In an embodiment, the PDE4 inhibitor combination is formulated as an orally dissolving strip ("film"), which rapidly dissolves in the mouth to release the active agent contained in the strip. The orally dissolving strips generally comprise a water soluble polymer and the active agents. Exemplary classes of water soluble polymers include water soluble cellulosic polymers, water soluble synthetic polymers, water soluble natural gums and polymers or derivatives thereof, or a combination thereof. Exemplary water soluble cellulosic polymers include hydroxypropyl cellulose, hydroxypropylmethyl cellulose, hydroxyethyl cellulose, carboxymethyl cellulose, or a combination thereof. Exemplary water soluble natural gums and polymers include amylose, dextran, casein, pullulan, gelatin, pectin, agar, carrageenan, xanthan gum, tragacanth, guar gum, acacia gum, arabic gum, sodium alginate, zein, or a combination thereof. Exemplary water soluble synthetic polymers include polyethylene glycol, polyethylene oxide, polyvinyl pyrrolidone, polyvinyl alcohol, carboxyvinyl polymers, water soluble polyacrylic acid/acrylate, or a combination thereof.

The orally dissolving strip can further optionally comprise a plasticizer in addition to the water soluble polymer and active agent. Exemplary plasticizers include propylene glycol, glycerin, glycerol, monoacetin, diacetin, triacetin, dimethyl phthalate, diethyl phthalate, dibutyl phthalate, dibutyl sebacate, triethyl titrate, tributyl citrate, triethyl citrate, triethyl acetyl citrate, castor oil, acetylated monoglycerides, sorbitol, or a combination thereof.

The orally dissolving strip can further optionally comprise an emulsifying agent in addition to the water soluble polymer and active agent. Exemplary emulsifying agents include polyvinyl alcohol, a sorbitan esters, a cyclodextrin, benzyl benzoate, glyceryl monostearate, a polyoxyethylene alkyl ether, a polyoxyethylene stearate, poloxamer, a polyoxyethylene castor oil derivative, a hydrogenated vegetable oil, a polysorbate, or a combination thereof.

The orally dissolving strip can further optionally comprise a flavorant or sweetener in addition to the water soluble polymer and active agent. Exemplary sweeteners include sugar, a monosaccharide, an oligosaccharide, aldose, ketose, dextrose, maltose, lactose, glucose, fructose, sucrose, a sugar polyol (e.g., mannitol, xylitol, sorbitol, erythritol, and the like), artificial sweeteners (e.g., acesulfame potassium, sucralose, aspartame, saccharin, sodium saccharin, and the like) or a combination thereof.

In some embodiments, the orally dissolving formulations of the present invention may comprise an additional excipient. Suitable additional excipients include, but are not limited to, microcrystalline cellulose, colloidal silicon dioxide, talc, starch, or a combination thereof. Other optional components that can be used to prepare the orally dissolving strip include a filler/diluent, a surfactant, a disintegrating agent, an antifoaming agent, an antioxidant, a buffering agent, a colorant, or a combination thereof.

A solvent can be used in the process to prepare the orally dissolving strip, including water, ethanol, 1-butanol, 2-butanol, 2-ethoxyethanol, ethyl acetate, methyl acetate, 3-methyl-1-butanol, methylethyl ketone, 2-methyl-1-propanol, isobutyl acetate, isopropyl acetate ethyl ether, tert-butylmethyl ether acetone, or a combination thereof. The solvent is used for processing and then removed to result in the final product.

Methods of preparing orally dissolving strips involve solvent casting and film coating. The active agent is mixed with film-forming excipients and solvents such as water, ethanol, and the like. A thin coating of the mixture is cast on a moving, inert substrate and the coated substrate is moved through a drying oven to evaporate the solvent before die-cutting the dried film into strips. Another method involves hot-melt extrusion, by melting an active agent and excipient polymer blend which is then extruded through a die under molten conditions. The thin film is then cooled to room temperature and die-cut into strips.

In one nonlimiting embodiment, the PDE4 combination is formulated as an oral liquid dosage form (solution, suspension, dispersion, etc.), or in a reconstitutable form that when combined with a pharmaceutically acceptable oral liquid carrier results in an oral liquid dosage form. The liquid dosage forms generally include the PDE4 inhibitor, an additional active agent, and a pharmaceutically acceptable oral liquid carrier (alternatively "pharmaceutically acceptable oral liquid vehicle"). Additional optional ingredients include a suspending agent, a sweetener, a flavoring agent, a preservative, a pH adjusting agent, a colorant, or a combination thereof.

The PDE4 inhibitor and additional active agent can be present in the liquid composition in free form or in the form of a coated or uncoated granule, microtablet, pellet (as used herein "pellet" means a spherical granule prepared by extrusion and spheronization, and is equivalent to bead, spheroid, and microsphere), particle, or other multiparticulate system. The coating can include film forming coating, a taste-masking coating, a controlled-release coating, and the like.

Suitable liquid carriers include, for example, water; glycerin; propylene glycol; a lower polyethylene glycol (e.g., polyethylene glycol 200, polyethylene glycol 300, polyethylene glycol 400, polyethylene glycol 540, polyethylene glycol 600, and the like); ethanol; propylene carbonate; or a combination thereof.

The suspending agent for use in the liquid composition include, for example, a carbomer, a cellulose derivative such as powdered cellulose, methylcellulose, a hydroxyl alkyl cellulose such as hydroxyethyl cellulose, hydroxypropyl cellulose, or hydroxypropyl methylcellulose, carboxy methyl cellulose calcium, carboxy methyl cellulose sodium, polyvinylpyrrolidone; a natural gum such as gum acacia, carrageenan, sodium alginate, gellam gum, gum ghatti, guar gum, locust bean gum, tragacanth, xanthan gum; or a combination thereof.

A sweetener can be included in the liquid composition to make the composition palatable and more pleasing to the patient and to mask the taste of the active agents. Exemplary sweeteners include sugar alcohols (or polyols), such as glycerol, sorbitol, xylitol, mannitol, galactitol, maltitol, hydrogenated isomaltulose (isomalt), lactitol, erythritol, glucitol, ribitol, or a combination thereof; sugar sweeteners generally include saccharides, such as mono-saccharides, di-saccharides and poly-saccharides such as sucrose (saccharose, sugar), dextrose, maltose, dextrin, maltodextrin, xylose, ribose, glucose (including liquid glucose), mannose, galactose, fructose (levulose), lactose, invert sugar, fructo oligo saccharide syrups, trehalose, tagatose, fucose, gulose, raffinose, ribulose, rufinose, stachyose, xylulose, adonose, amylase, arabinose, deoxyribose, corn syrup solids, such as high fructose corn syrup, or a combination thereof; artificial sweeteners such as soluble saccharin salts, i.e., sodium or calcium saccharin salts, the potassium salt of 3,4-dihydro-6-methyl-1,2,3-oxathiazine-4-one-2,2-dioxide (Acesulfame-K), the free acid form of saccharin, L-aspartic acid derived sweeteners, such as L-aspartyl-L-phenylalanine methyl ester (Aspartame), L-alphaaspartyl-N-(2,2,4,4-tetramethyl-3-thietanyl)-D-alaninamide hydrate (Alitame), N—[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, or a combination thereof; maltol; or a combination thereof.

The liquid composition may optionally further comprise a flavoring agent. Flavoring agents include those flavors known to one of ordinary skill in the art, such as natural flavors and artificial flavors. Suitable amounts of flavoring agent can be selected by one of ordinary skill in the art without undue experimentation.

In an embodiment, the liquid composition can further include a preservative to prevent the unwanted growth of bacteria, molds, fungi, or yeast. Examples of suitable preservatives include benzoic acid alkali metal salts (e.g., sodium benzoate), sorbic acid alkali metal salts (e.g., potassium sorbate), sodium erythorbate, sodium nitrite, calcium sorbate, butylated hydroxyanisole (BHA), butylated hydroxytoluene (BHT), parabens (e.g., lower alkyl esters of para-hydroxybenzoic acid), alkali metal salts of parabens including sodium and potassium salts of methyl-, ethyl-, propyl-, or butylparaben, or a combination thereof. Specific preservatives include sodium methylparaben, sodium propylparaben, and sodium butylparaben.

In one nonlimiting embodiment, the oral liquid composition is preservative free.

The liquid composition optionally further comprises a colorant conventional in the pharmaceuticals art. Colorants can be used in amounts effective to produce a desired color for the composition. The colorants may include pigments, natural food colors, and dyes suitable for pharmaceutical applications.

The liquid composition optionally further includes a buffering agent or a pH adjusting agent to render the final liquid composition to a targeted pH. Suitable pH adjusting agents include pharmaceutically acceptable acids, bases, and their salts. Exemplary pH adjusting agents include alkali metal hydroxides (e.g., sodium hydroxide and potassium hydroxide), hydrochloric acid, alkali metal carbonates (e.g., sodium carbonate and potassium carbonate), carbonic acid, or a combination thereof. The pH adjusting agents can be used as solutions or suspensions in a pharmaceutically acceptable solvent. Suitable pharmaceutically acceptable solvents for use with the pH adjusting agent can include purified water, lower alkyl alcohols such as ethanol, a glycol, and the like, or a combination thereof.

In another nonlimiting embodiment, the combination of PDE4 inhibitor and an additional active agent is formulated in a powder form for single use, such as a sachet, to be suspended in a liquid carrier such as water or saliva. The powder form can be added to a glass of water with stirring or taken directly in the mouth where the ingredients are suspended in saliva and then swallowed.

In another nonlimiting embodiment, the combination of PDE4 inhibitor and an additional active agent is formulated in a powder form for multiple use, such as powder for suspensions in a bottle. A specified amount of water or a flavored solution can be added to constitute a suspension that is enough for multiple doses.

General components in the powder formulation include the active agents, a sweetener, and a suspending agent; optionally further comprising a flavorant, a colorant, a disintegrant, a combination thereof, and the like.

Those forms existing as liquids (e.g., solution, emulsion, or suspension) can be packaged for convenient dosing in prepackaged, single use containers, or in containers comprising multiple doses.

The following nonlimiting examples are provided to further illustrate the present invention.

EXAMPLES

Example 1: Preparation of Rolipram 250 mg and Naproxen Sodium, 220 mg Immediate Release Tablet Formulation

| Component | Mg/Tab |
|---|---|
| Base granules | |
| Rolipram | 250 |
| Naproxen Sodium | 220 |
| Plasdone K29/32 | 10 |
| Purified Water | * |
| Compression Mix | |
| Base granules | 480 |
| Microcrystalline cellulose (Avicel PH 101) | 217 |
| Hydroxy propylcellulose (Klucel EXF) | 30 |
| Polyplasdone XL | 15 |
| Magnesium Stearate | 8 |
| Total | 750 |

* not in final formulation

Rolipram and Naproxen Sodium were weighed. Plasdone K29/32 was dissolved in water. Rolipram and Naproxen Sodium were then granulated with the Plasdone K29/32 solution. The granules were then dried in an oven at 50° C. and milled using a suitable mill. The Avicel PH 101, Klucel EXF and Polyplasdone XL were passed through a #20 mesh screen. The screened materials were then blended with the milled Rolipram and Naproxen Sodium granules. The magnesium stearate was passed through a #30 mesh screen. The screened magnesium stearate was then added to the above blend and mixed well. 750 mg of the blend was compressed to make Rolipram and Naproxen Sodium immediate release tablets comprising 250 mg of Rolipram and 200 mg of Naproxen.

Example 2: Preparation of Rolipram 250 mg and Zolpidem Tartrate 5 mg Immediate Release Tablet Formulation

| Component | Mg/Tab |
|---|---|
| Base granules | |
| Rolipram | 250 |
| Zolpidem Tartrate | 5 |
| PVP K29/32 | 3 |
| Purified water | * |
| Compression Mix | |
| Base granules | 258 |
| Microcrystalline cellulose (Avicel PH 101) | 60 |
| Hydroxy propylcellulose (Klucel EXF) | 5 |
| Lactose mono hydrate | 70 |
| Croscarmellose Sodium (Ac-Di-Sol) | 6 |
| Magnesium Stearate | 1 |
| Total | 400 |

* not in final formulation

Rolipram and Zolpidem Tartrate were weighed. Plasdone K29/32 was dissolved in purified water. Rolipram and Zolpidem Tartrate were granulated with Plasdone K29/32 solution. The granules were dried in an oven at 50° C. and milled using a suitable mill. Avicel PH 101, Klucel EXF, lactose monohydrate and Ac-Di-Sol were passed through a #20 mesh screen. The screened materials were then blended with milled Rolipram and Zolpidem granules. Magnesium stearate was passed through a #30 mesh screen. The screened magnesium stearate was added to the above blend and mixed well. 400 mg of the blend was compressed to make Rolipram 250 mg and Zolpidem tartrate 5 mg immediate release tablets.

Example 3: Preparation of Cilomilast 15 mg and Fluoxetine HCl, 20 mg Immediate Release Capsule Formulation

| Component | Mg/Cap |
|---|---|
| Base granules | |
| Cilomilast | 15 |
| Fluoxetine HCl | 20 |

-continued

| Component | Mg/Cap |
|---|---|
| Microcrystalline cellulose (Avicel PH 200) | 60 |
| PVP K29/32 | 5 |
| Purified water | * |
| Compression Mix | |
| Base granules | 100 |
| Microcrystalline cellulose (Avicel PH 200) | 70 |
| Lactose mono hydrate | 74 |
| Croscarmellose Sodium (Ac-Di-Sol) | 5 |
| Magnesium Stearate | 1 |
| Total | 250 |

* not in final formulation

Cilomilast, Fluoxetine HCl and Avicel were weighed. Plasdone K29/32 was dissolved in purified water. Cilomilast, Fluoxetine HCl and Avicel were granulated with Plasdone K29/32 solution. The granules were dried in an oven at 50° C. and milled using a suitable mill. Avicel PH 200, lactose monohydrate and Ac-Di-Sol were passed through a #20 mesh screen. The screened materials were then blended with milled Cilomilast, Fluoxetine HCl and Avicel granules. Magnesium stearate was passed through a #30 mesh screen. The screened magnesium stearate was added to the above blend and mixed well. 250 mg of the blend encapsulated to make Cilomilast 15 mg and Fluoxetine HCL 20 mg immediate release capsules.

Example 4: Preparation of Naproxen Sodium, 300 mg Extended Release Tablet Formulation

| Component | Mg/Tab |
|---|---|
| Base granules | |
| Naproxen Sodium | 330 |
| Carnauba wax | 210 |
| Ethyl cellulose powder | 50 |
| Stearic acid | 50 |
| SD3A Alcohol | * |
| Compression Mix | |
| Base granules | 640 |
| Silicon Dioxide (Syloid 244 FP) | 5 |
| Magnesium Stearate | 5 |
| Total | 650 |

* not in final formulation

Naproxen sodium, carnauba wax and ethyl cellulose powder were mixed. Stearic acid was dissolved in SD3A alcohol by heating the alcohol to 50° C. The powder mix was granulated with stearic acid solution. The granules were dried in an oven at 35° C. and milled using a suitable mill. Syloid was passed through a #20 mesh screen. The milled granules and screened Syloid were blended in a blender. Magnesium stearate was passed through a #30 mesh screen. The screened magnesium stearate was added to the blender and mixed well. 650 mg of the blend was compressed to make Naproxen Sodium extended release tablets comprising 300 mg of Naproxen.

Example 5: Preparation of Roflumilast 250 mcg and Naproxen Sodium, 500 mg Bi-Layer Immediate/Extended Release Tablets

| Component | Mg/Tab |
|---|---|
| Base granules | |
| Roflumilast | 0.25 |
| Naproxen Sodium | 220 |
| Plasdone K29/32 | 4.75 |
| Purified Water | * |
| Compression Mix | |
| Base granules | 225 |
| Microcrystalline cellulose (Avicel PH 101) | 57 |
| Hydroxy propylcellulose (Klucel EXF) | 5 |
| Polyplasdone XL | 10 |
| Magnesium Stearate | 3 |
| Total | 300 |

* not in final formulation

Roflumilast and Naproxen Sodium were weighed. Plasdone K29/32 was dissolved in water. Roflumilast and Naproxen Sodium was then granulated with the Plasdone K29/32 solution. The granules were then dried in an oven at 50° C. and milled using a suitable mill. The Avicel PH 101, Klucel EXF and Polyplasdone XL were passed through a #20 mesh screen. The screened materials were then blended with the milled Roflumilast and Naproxen Sodium granules. The Magnesium stearate was passed through a #30 mesh screen. The screened Magnesium Stearate was then added to the above blend and mixed well.

300 mg of the blend was compressed with 650 mg of extended release formulation blend prepared as per Example 4 into bi-layer tablets using an alternative tablet press. Each tablet contained 250 mcg of Roflumilast and 500 mg of Naproxen.

Example 6: Preparation of Roflumilast 500 mcg and Esomeprazole 20 mg Capsule Formulation

| Component | Mg/Cap |
|---|---|
| Roflumilast | 0.5 |
| Lactose mono hydrate | 89.5 |
| Microcrystalline cellulose (Avicel PH 101) | 70 |
| PVP K29/32 | 8 |
| Purified water | * |
| Croscarmellose Sodium (Ac-Di-Sol) | 6 |
| Magnesium Stearate | 1 |
| Esomeprazole Enteric coated granules (equivalent to 20 mg of Esomeprazole) | 75 |
| Total | 250 |

* not in final formulation

Roflumilast, Avicel PH 101 and Lactose monohydrate were weighed. Plasdone K29/32 was dissolved in purified water. S Roflumilast, Avicel PH 101 and Lactose monohydrate were granulated with Plasdone K29/32 solution. The granules were dried in an oven at 50° C. and milled using a suitable mill. Ac-Di-Sol was passed through a #20 mesh screen. The screened materials were then blended with milled Roflumilast granules. Esomeprazole Enteric coated granules (equivalent to 20 mg of Esomeprazole) were added to Roflumilast granules and blended. Magnesium stearate was passed through a #30 mesh screen. The screened Magnesium Stearate was added to the above blend and mixed well. 250 mg of the blend encapsulated to make Roflumilast 500 mcg and Esomeprazole 20 mg capsules.

Example 7: Preparation of Apremilast 10 mg and Bismuth Subsalicylate 525 mg Per 30 mL Suspension

| Component | Mg/30 mL |
|---|---|
| Apremilast | 10 |
| Bismuth Subsalicylate | 525 |
| Xanthan Gum | 100 |
| Benzoic Acid | 25 |
| Sodium Saccharin | 50 |
| D&C Red 22 | 1 |
| D&C Red 28 | 0.5 |
| Mint flavor | 120 |
| Purified Water | 28000 |

Weigh approximately two thirds of Purified water in main SS vessel. Slowly add Xanthan Gum and mix until fully hydrated. In a separate vessel take the rest of Purified water and disperse sodium saccharin, benzoic acid, Apremilast and Bismuth Subsalicylate. Transfer the drug dispersion to Xanthan gum solution and mix thoroughly. Homogenize the suspension if needed. Add and dissolve color and flavor.

Example 8: Preparation of Ibudilast 30 mg and Ondansetron, 4 mg Immediate Release Capsule Formulation

| Component | Mg/Cap |
|---|---|
| Base granules | |
| Ibudilast | 30 |
| Ondansetron | 4 |
| Microcrystalline cellulose (Avicel PH 200) | 62 |
| PVP K29/32 | 4 |
| Purified water | * |
| Compression Mix | |
| Base granules | 100 |
| Microcrystalline cellulose (Avicel PH 200) | 70 |
| Lactose mono hydrate | 74 |
| Croscarmellose Sodium (Ac-Di-Sol) | 5 |
| Magnesium Stearate | 1 |
| Total | 250 |

* not in final formulation

Ibudilast, Ondansetron and Avicel were weighed. Plasdone K29/32 was dissolved in purified water. Ibudilast, Ondansetron and Avicel were granulated with Plasdone K29/32 solution. The granules were dried in an oven at 50° C. and milled using a suitable mill. Avicel PH 200, Lactose monohydrate and Ac-Di-Sol were passed through a #20 mesh screen. The screened materials were then blended with milled Ibudilast, Ondansetron and Avicel granules. Magnesium stearate was passed through a #30 mesh screen. The screened Magnesium Stearate was added to the above blend and mixed well. 250 mg of the blend encapsulated to make Ibudilast 30 mg and Ondansetron 4 mg immediate release capsules.

Example 9: Preparation of Roflumilast 250 mcg and Loperamide HCl, 2 mg Immediate Release Tablets

| Component | Mg/Cap |
|---|---|
| Base granules | |
| Roflumilast | 0.25 |
| Loperamide HCl | 2 |
| Microcrystalline cellulose (Avicel PH 200) | 92.75 |
| PVP K29/32 | 5 |
| Purified water | * |
| Compression Mix | |
| Base granules | 100 |
| Microcrystalline cellulose (Avicel PH 200) | 70 |
| Lactose mono hydrate | 74 |
| Croscarmellose Sodium (Ac-Di-Sol) | 5 |
| Magnesium Stearate | 1 |
| Total | 250 |

* not in final formulation

Roflumilast, Loperamide HCl and Avicel were weighed. Plasdone K29/32 was dissolved in purified water. Roflumilast, Loperamide HCl and Avicel were granulated with Plasdone K29/32 solution. The granules were dried in an oven at 50° C. and milled using a suitable mill. Avicel PH 200, Lactose monohydrate and Ac-Di-Sol were passed through a #20 mesh screen. The screened materials were then blended with milled Roflumilast, Loperamide HCl and Avicel granules. Magnesium stearate was passed through a #30 mesh screen. The screened Magnesium Stearate was added to the above blend and mixed well. 250 mg of the blend is compressed to make Roflumilast 250 mcg and Loperamide HCL 2 mg immediate release tablets.

Example 10: Preparation of Cilomilast 15 mg and Rifaximin, 550 mg Immediate Release Tablets

| Component | Mg/Cap |
|---|---|
| Base granules | |
| Cilomilast | 15 |
| Rifaximin | 550 |
| PVP K29/32 | 10 |
| Purified water | * |
| Compression Mix | |
| Base granules | 575 |
| Microcrystalline cellulose (Avicel PH 200) | 70 |
| Lactose mono hydrate | 74 |
| Croscarmellose Sodium (Ac-Di-Sol) | 5 |
| Magnesium Stearate | 1 |
| Total | 725 |

* not in final formulation

Cilomilast and Rifaximin were weighed. Plasdone K29/32 was dissolved in purified water. Cilomilast and Rifaximin were granulated with Plasdone K29/32 solution. The granules were dried in an oven at 50° C. and milled using a suitable mill. Avicel PH 200, Lactose monohydrate and Ac-Di-Sol were passed through a #20 mesh screen. The screened materials were then blended with milled Cilomilast and Rifaximin granules. Magnesium stearate was passed through a #30 mesh screen. The screened Magnesium Stearate was added to the above blend and mixed well. 725 mg of the blend compressed to make Cilomilast 15 mg and Rifaximin 550 mg immediate release tablets.

Example 11: Preparation of Ibudilast 30 mg and Prednisone, 5 mg Immediate Release Capsules

| Component | Mg/Cap |
|---|---|
| Base granules | |
| Ibudilast | 30 |
| Prednisone | 5 |
| Microcrystalline cellulose (Avicel PH 200) | 60 |
| PVP K29/32 | 5 |
| Purified water | * |
| Compression Mix | |
| Base granules | 100 |
| Microcrystalline cellulose (Avicel PH 200) | 70 |
| Lactose mono hydrate | 74 |
| Croscarmellose Sodium (Ac-Di-Sol) | 5 |
| Magnesium Stearate | 1 |
| Total | 250 |

* not in final formulation

Ibudilast, Prednisone and Avicel were weighed. Plasdone K29/32 was dissolved in purified water. Ibudilast, Prednisone and Avicel were granulated with Plasdone K29/32 solution. The granules were dried in an oven at 50° C. and milled using a suitable mill. Avicel PH 200, Lactose monohydrate and Ac-Di-Sol were passed through a #20 mesh screen. The screened materials were then blended with milled Ibudilast, Prednisone and Avicel granules. Magnesium stearate was passed through a #30 mesh screen. The screened Magnesium Stearate was added to the above blend and mixed well. 250 mg of the blend encapsulated to make Ibudilast 30 mg and Prednisone 5 mg immediate release capsules.

Example 12: Bi-Layer Immediate/Extended Release Tablets Comprising 500 mcg of Roflumilast, 20 mg of Esomeprazole and 500 mg of Naproxen

| Component | Mg/Tab |
|---|---|
| Roflumilast | 0.5 |
| Naproxen Sodium | 220 |
| Lactose mono hydrate | 75 |
| Microcrystalline cellulose (Avicel PH 101) | 64.5 |
| PVP K29/32 | 8 |
| Purified water | * |
| Croscarmellose Sodium (Ac-Di-Sol) | 6 |
| Magnesium Stearate | 1 |
| Esomeprazole Enteric coated granules (equivalent to 20 mg of Esomeprazole) | 75 |
| Total | 450 |

* not in final formulation

Roflumilast, Naproxen Sodium, Avicel PH 101 and Lactose monohydrate were weighed. Plasdone K29/32 was dissolved in purified water. Roflumilast, Naproxen Sodium, Avicel PH 101 and Lactose monohydrate were granulated with Plasdone K29/32 solution. The granules were dried in an oven at 50° C. and milled using a suitable mill. Ac-Di-Sol was passed through a #20 mesh screen. The screened materials were then blended with milled Roflumilast and Naproxen granules. Esomeprazole Enteric coated granules (equivalent to 20 mg of Esomeprazole) were added to Roflumilast and Naproxen granules and blended. Magnesium stearate was passed through a #30 mesh screen. The screened Magnesium Stearate was added to the above blend and mixed well.

450 mg of the final blend was compressed with 650 mg of blend prepared according to Example 4 into bi-layer tablets using an alternative tablet press. Each tablet contained 500 mcg of Roflumilast, 20 mg of Esomeprazole and 500 mg of Naproxen.

What is claimed is:

1. A composition for oral administration comprising an immediate release phosphodiesterase-4 (PDE4) inhibitor and an additional active agent configured for modified release that reduces or eliminates a side effect associated with the selected PDE4 inhibitor, wherein the additional active agent is an anti-nausea agent, an antiemetic, an appetite stimulant, or any combination thereof,
   wherein release and duration of the additional active agent is modified to correlate with pharmacokinetic characteristics of half-life and median time for maximum concentration for the selected PDE4 inhibitor and to effectively manage a reduction or elimination of the side effect, and
   wherein the side effect is nausea, vomiting or weight loss.

2. The composition of claim 1 wherein the PDE4 inhibitor is Roflumilast, Apremilast, Crisaborole, Cilomilast, Ronomilast, Oglemilast, Rolipram, Ibudilast, Tetomilast, Revamilast, Roflumilast, Tofimilast, Almiral, Lotamilast, a pharmaceutically acceptable salt thereof or a combination thereof.

3. The composition of claim 1, wherein the controlled release is achieved with a controlled release matrix, a functional coating, or a combination thereof; and wherein the controlled release is extended release, delayed release, pulsed release, or a combination thereof.

4. The composition of claim 1 formulated as a solid, semisolid, or liquid formulation.

5. The composition of claim 1 formulated as a tablet, a capsule, a pellet, a film, a sachet, a powder, a chewable gummy, a solution, a suspension, or an emulsion.

6. The composition of claim 1 wherein the PDE4 inhibitor is Roflumilast.

7. The composition of claim 1 formulated to release Roflumilast as immediate release.

8. The composition of claim 6 wherein the additional active agent is Dronabinol.

9. The composition of claim 6 wherein the additional active agent is Dronabinol.

10. A method for treating a condition treatable with a PDE4 inhibitor therapy, said method comprising orally administering to a subject in need thereof the composition of claim 1.

11. A method for increasing patient compliance with treatment with a selected PDE4 inhibitor, said method comprising orally administering to a patient the composition of claim 1.

\* \* \* \* \*